United States Patent [19]

Wojtkowski

[11] Patent Number: 4,605,790

[45] Date of Patent: Aug. 12, 1986

[54] PHENOL FROM COAL AND BIOMASS

[75] Inventor: Paul W. Wojtkowski, Wilmington, Del.

[73] Assignee: E. I. Du Pont de Nemours and Company, Wilmington, Del.

[21] Appl. No.: 736,385

[22] Filed: May 21, 1985

[51] Int. Cl.$^4$ ............................................. C07C 37/68
[52] U.S. Cl. ................................... 568/750; 568/783; 568/805
[58] Field of Search .................... 568/750, 805, 783

[56] References Cited

U.S. PATENT DOCUMENTS

| 3,284,513 | 11/1966 | Dedinas | 568/805 |
| 3,284,514 | 11/1966 | Dedinas | 568/805 |
| 3,700,745 | 10/1972 | Kovach et al. | 568/805 |
| 3,963,602 | 6/1976 | Wright | 568/805 |
| 4,189,613 | 2/1980 | Bjoroson | 568/805 |
| 4,191,844 | 3/1980 | Bjoroson | 568/805 |
| 4,230,895 | 10/1980 | Daly | 568/805 |
| 4,230,896 | 10/1980 | Daly | 568/805 |
| 4,283,571 | 8/1981 | Kim et al. | 561/783 |
| 4,465,892 | 8/1984 | Jacobs et al. | 568/783 |
| 4,503,269 | 3/1985 | Engel et al. | 568/783 |

Primary Examiner—Werren B. Lone

[57] ABSTRACT

Phenol is prepared from mixed phenols derived from coal or biomass by separation of the mixed phenols, isomerization of m- and/or p-cresols to o-cresol, demethylation of o-cresol, dealkylation of xylenols and other alkyl phenols, recycling of products other than phenol, and, optionally, reducing phenol to cyclohexanone/cyclohexanol, followed by oxidation thereof to adipic acid.

18 Claims, 2 Drawing Figures

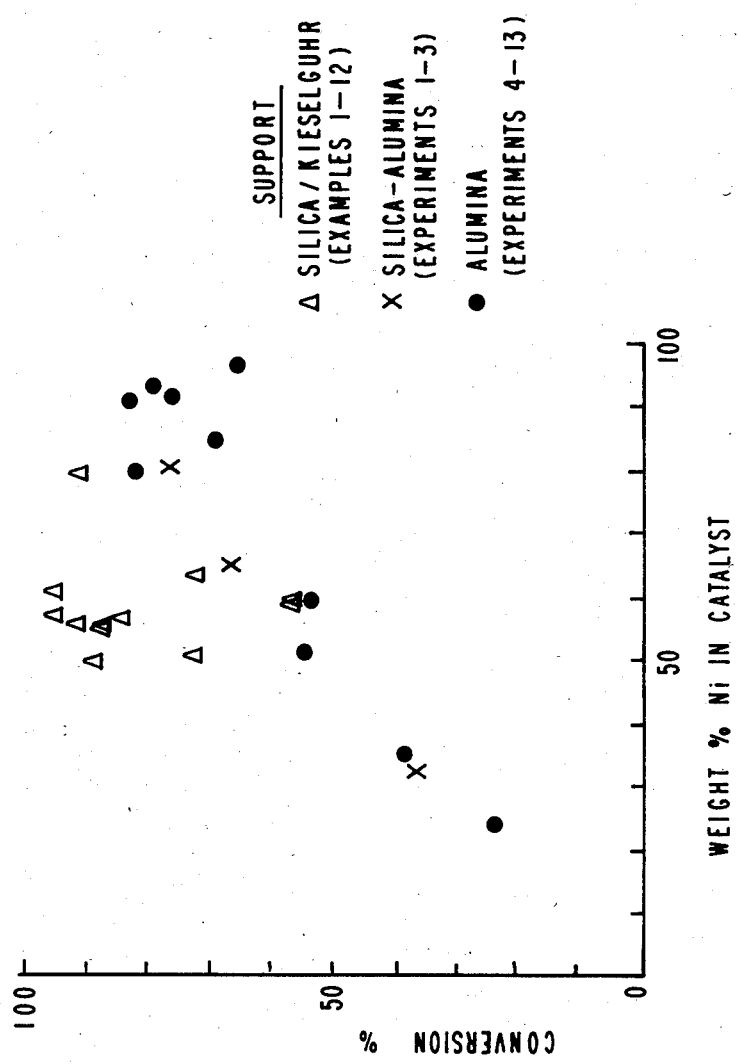

PHENOL FROM COAL AND BIOMASS

FIELD OF THE INVENTION

This invention relates to the preparation of phenol from mixed alkyl phenols, such as can be derived from coal and biomass, and to the preparation of adipic acid from the phenol so prepared.

BACKGROUND OF THE INVENTION

Phenol is an important chemical having a wide variety of uses. Included among these is the preparation of adipic acid, a nylon precursor. Utilization of phenol for this and other uses is increasing. Phenol is currently derived principally from petroleum. Due to the potentially increasing scarcity and cost of petroleum, alternative sources therefor are highly desirable.

It is known that polymeric aromatic compounds, particularly peat, coal and lignin, which are in relatively abundant supply, can be depolymerized to yield varying amounts of mixed phenols. Coal is a complex, multi-ring, aromatic polymer with varying relative amounts of carbon, oxygen and hydrogen. Of most significance to phenol production are bituminous, sub-bituminous and lignite coals. Coal depolymerization techniques include liquefaction, gasification and pyrolysis.

Lignin is essentially a polyphenol having a high oxygen content. It is derivable from biomass, i.e., renewable resources such as trees, agricultural products and municipal waste, by a variety of processes. These include, e.g., the well-known Kraft process and acidic hydrolysis. The exact composition of lignin so derived, and hence possibly the desirability of the lignin for use in producing phenols, depends upon both the source of the lignin and the manner in which it is derived therefrom.

Mixed phenols derived from coal and biomass can, depending on the source and the depolymerization process, comprise phenol, cresols, xylenols and higher alkyl and polyalkyl phenols, such as ethyl phenol and propyl phenol, in varying relative amounts. Reported or projected mixed phenol compositions from various coal and lignin sources by various depolymerization techniques appear in Table 1, which follows, in weight percent. In the first column, the mixed phenols are reported as weight percents of all crude tar acid products. In the other columns, they are reported as weight percents of all mixed phenol products.

TABLE 1

| | Gasification | | Lique-faction Bituminous Coal[3] | Hydro-cracking Kraft Lignin[4] |
|---|---|---|---|---|
| | S. Afr. (SASOL) Coal[1] | subbituminous Coal[2] | | |
| phenol | 38 | 18 | 38 | 7 |
| o-cresol | 8 | 9 | 10 | 4 |
| m-, p-cresol | 14 | 16 | 31 | 22 |
| xylenols | 13 | 14 | 9 | 7 |
| other alkyl phenols | 16 | 42 | 12 | 61 |

[1]Hoogendoorn, J.C. IGT Symposium Papers on Clean Fuels from Coal, Sept. 1973, page 111.
[2]Frank, M.A., IGT Symposium Papers Advance in Coal Utilization Technology III, May 1979, page 727.
[3]Gulf Mineral Resources Company, personal communication.
[4]Parkhurst, H.J., et al., Symposium on Alternate Feedstocks for Petrochemicals, ACS Meeting, Las Vegas, Nevada, August 1980.

Various dealkylation procedures for converting such mixed phenols to phenol are known. These include thermal dealkylation procedures such as are disclosed in the following: U.S. Pat. No. 4,230,895 which discloses a process for thermal hydrodealkylation of mixed alkyl phenols; U.S. Pat. No. 3,284,513 which discloses a process for thermal hydrodealkylation of monoalkylated phenols; and U.S. Pat. No. 3,284,514 which discloses a process for thermal hydrodealkylation of polyalkylated phenols. The Hydrocarbon Research, Inc. Dynaphen process, Chem. and Eng. News, Nov. 30, 1981, pages 32,34, is an example of a thermal dealkylation procedure using coal liquids.

U.S. Pat. No. 4,191,844 discloses a catalytic process for hydrodealkylating certain aromatic compounds in a single vessel, in which process the catalyst contains manganese oxide and a Group IIA metal oxide for dealkylation and transalkylation; a Group VIII metal oxide, such as nickel oxide, to allow dealkylation at lower temperature; and alumina or silica-alumina containing a major amount of alumina for isomerization of m-cresol to o-cresol. The patent further discloses that cresols and xylenols can be derived from coal.

U.S. Pat. No. 4,189,613 discloses catalytic hydrodealkylation of certain aromatic compounds in which the catalyst is a low sodium-content chromia on alumina.

U.S. Pat. No. 4,436,945 discloses catalytic hydrodealkylation of alkyl aromatic compounds using a zeolite catalyst wherein 15 to 50 equivalent % of exchangeable cations have been exchanged for hydrogen ions.

U.S. Pat. No. 4,405,812 discloses a process for dealkylating ortho-alkylated aromatic amines at elevated temperatures using a nickel catalyst, optionally supported on oxides, including silica, Kieselguhr, silica-alumina, alumina and magnesia.

Catalytic dealkylation procedures also include processes such as are disclosed in the following: Kadlec, J. and Bazant, V., Coll. Czech. Chem. Comm., 26, 1201–1203 (1961), which discloses dealkylation of o-ethyl and o-propyl phenols by catalytic hydrogenation; Jost. F. and Bazant, V., ibid., 3020–3027, which discloses demethylation of cresols; and Beranek, L., et al., Coll. Czech. Chem. Comm., 29, 239–249 (1964), which discloses dealkylation of various mono- and dialkyl phenols.

In the above-cited paper by Jost, F. and Bazant, V., it is disclosed that o-cresol is more highly reactive than m- and p-cresol. Publications disclosing demethylation of o-cresol include Jost and Bazant, supra; Weidenhoffer, Z., et al., Coll. Czech. Chem. Comm., 32, 3746–3756 (1967); Kadlec, J., et al., Coll. Czech. Chem. Comm., 26, 818 (1961); and Czechoslovakian Patent 99012, the latter disclosing a process for preparing a nickel-Group II, III or IV metal catalyst which is useful in dealkylating alkyl phenols.

U.S. Pat. No. 4,283,571 discloses a process for isomerizing o-cresol to m-cresol by contacting the o-cresol with a crystalline aluminosilicate zeolite of the ZSM type.

U.S. Pat. No. 4,465,892 discloses isomerization of hydrocarbons at a temperature of 100°–300° C. using a catalyst comprising a Group VIII metal supported on a bridged clay.

U.S. Pat. No. 4,503,269 discloses an improved process for isomerizing cresols in the presence of a crystalline aluminosilicate zeolite catalyst and added hydrogen, at a temperature in the range 250° C. to 450° C. and a pressure in the range of 2 to about 75 atmospheres. Hydrogen is present in a $H_2$/cresol mole ratio of about 1:1 to about 10:1. The isomerization of o-cresol to m- and p-cresols is emphasized and there is no showing or suggestion of enrichment of o-cresol.

U.S. Pat. No. 4,452,915 discloses a process for selective o-alkylation of phenols with a lower alkane in the presence of a supported nickel oxide catalyst. Supports include alumina, silica and Kieselguhr.

It is an object of this invention to provide a process for preparing phenol from mixed phenols. It is also an object to provide a process for preparing phenol from mixed phenols derived from coal and biomass. It is a further object of this invention to provide a process for preparing adipic acid from mixed phenols, such as may be derived from coal and biomass.

BRIEF DESCRIPTION OF THE DRAWINGS

FIG. 2 is a plot of conversion versus percent nickel in the catalyst based on data from Examples 1 to 12, within the invention, and Experiments 1 to 13, outside the invention.

DETAILED DESCRIPTION OF THE INVENTION

Figure 1:
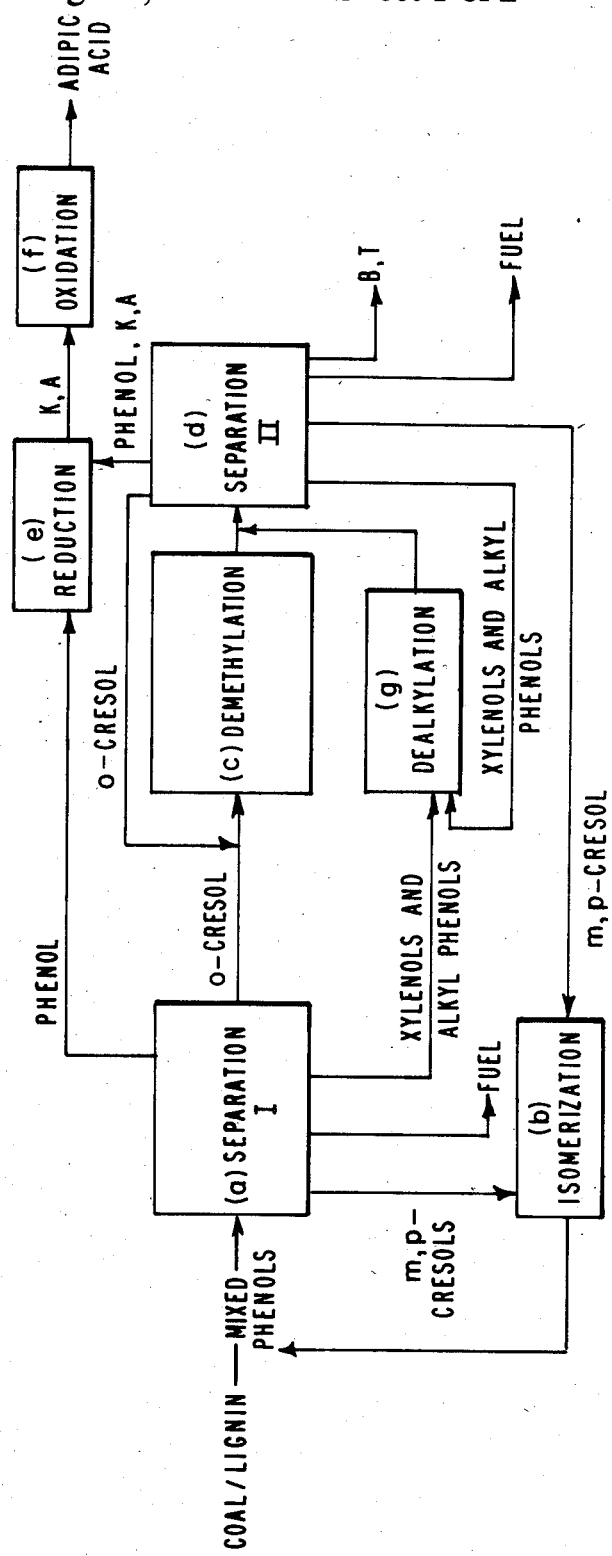
FIG. 1 is a flowsheet illustrating the process of the invention.

For further comprehension of the invention and of the objects and advantages thereof, reference may be made to the following description and to the appended claims in which the various novel features of the invention are more particularly set forth.

The invention resides in a process for preparing phenol from mixed phenols, which process comprises: (a) separating the mixed phenols; (b) isomerizing m- and/or p-cresols from (a) to o-cresol in a first vessel; and (c) demethylating o-cresol from (a) and (b) to phenol in a second vessel.

The invention further resides in said process wherein the product phenol is reduced, to yield cyclohexanone (K) and cyclohexanol (A) which are oxidized to adipic acid, and in said process wherein the mixed phenol starting material is derived from polymeric materials having aromatic structures, such as peat, coal and/or lignin.

By "comprises" is meant that the described process includes the enumerated steps but may also include additional steps, e.g., processing of xylenols and higher alkyl phenols, such as is suggested below, and separating and processing of a fuel fraction from the mixed phenols. Other additional steps, including, e.g., purification procedures, will be apparent to persons skilled in the art.

The phrase "mixed phenols" means a mixture comprising at least o-cresol and m-, p-cresols, i.e., o-cresol and m- and/or p-cresols. Mixed phenols are conveniently derived from coal or lignin and, therefore, will typically contain, in addition to o-cresol and m- and/or p-cresols, phenol, xylenols and higher alkyl phenols. Preferably, the mixed phenols used in the process of the invention are rich in phenol and cresols, such as the mixed phenols described in the third column of Table 1. Preferred coals include bituminous, sub-bituminous and lignite coals. Other polymeric materials having aromatic structures which may be converted to mixed phenols may also be useful as a source material.

With reference to FIG. 1, at the extreme upstream end, the process begins with depolymerization of lignin, derived from biomass, or of coal or peat, to mixed phenols. They undergo separation I, in process step (a), into various fractions. Distillation of mixed phenols allows convenient separation into fractions predominantly containing phenol, o-cresol, xylenols and other alkyl phenols, fuels and m- and/or p-cresols. The phenol fraction is desired product and can be collected and purified by known techniques.

The m- and/or p-cresols fraction undergoes conversion to o-cresol in step (b). The conversion is by catalytic isomerization, which preferably is carried out in the presence of an acidic crystalline aluminosilicate zeolite catayst, and during which, depending upon the catalyst employed, transalkylation will occur to a greater or lesser extent. The ZSM-type catalysts, particularly H+-ZSM-5, are preferred because these result in less coking and less transalkylation which produces undesired xylenols. ZSM-type catalysts are disclosed in U.S. Pat. No. 4,283,571 as having a pore dimension greater than about 5 Angstroms, pore windows of a size such as would be provided by a 10-membered ring of oxygen atoms, and a constraint index of from 1 to 12. The isomerization/transalkylation step is illustrated by Example 14 which resulted in a yield of 33 mol percent o-cresol and 3 mol percent phenol, using a ZSM-5 catalyst. The isomerization procedure illustrated by Example 14 can also be carried out in the liquid phase, i.e., under pressure, and without hydrogen, e.g., under conditions similar to those disclosed in U.S. Pat. No. 4,283,571 except that m- and/or p-cresol is used instead of o-cresol. Such a liquid phase procedure may be preferable to the illustrated gas phase procedure of Example 14.

The products from step (b) are recycled through step (a), separation I, and are separated, as are the mixed phenols. The o-cresol from separation I, which includes the o-cresol from step (b), undergoes demethylation in step (c) to convert the o-cresol to phenol and, subsequently if desired, determined by the conditions, to K and A.

The demethylation step (c) is carried out in the presence of catalyst consisting essentially of nickel and silica and/or Kieselguhr (diatomaceous silica) wherein the gram atomic Ni/Si ratio is about 0.2 to about 20, preferably about 0.5 to about 5, most preferably about 1 to about 2. These ratios correspond, respectively, to about 26 to about 95 wt % Ni, about 33 to about 83 wt % Ni and about 49 to about 66 wt % Ni. Such catalysts are commercially available or can be prepared by known methods, for example, by treating a mixture of nickel oxides or hydroxides and silica with hydrogen, as described in U.S. Pat. No. 4,251,394. Demethylation can also be achieved with nickel/alumina or nickel/silica-alumina catalysts of the art (Experiments 1 to 13).

Nickel/silica and/or Kieselguhr catalysts used in the present invention are superior to the nickel/alumina and nickel/silica-alumina catalysts of the art for the demethylation of o-cresol, the latter two catalysts being outside the invention. Nickel/silica and/or Kieselguhr catalysts, when compared to nickel/alumina and nickel/silica-alumina catalysts having approximately the same nickel content by weight, provide higher conversions of o-cresol and higher yields of phenol under similar reaction conditions (FIG. 2 and Table 6). Moreover, even at higher contents of the expensive nickel component, the alumina or silica-alumina supported catalysts show inferior conversions and phenol yields as compared to the silica- and/or Kieselguhr-supported catalysts of significantly lower nickel content (FIG. 2 and Table 7). The latter also provide higher yields of benzene and toluene in the co-products (Tables 6 and 7); these chemicals are particularly desirable intermediates. Furthermore, the catalysts used in the process of this invention result in fewer undesirable isomerized and transalkylated by-products, such as m- and p-cresols and xylenols. Selectivity to phenol is approximately equivalent with all the catalysts (Tables 3B, 4B and 5).

The lifetime of nickel/silica and/or Kieselguhr catalysts is also superior to nickel catalysts supported on alumina or silica-alumina in o-cresol demethylation under similar reaction conditions, as shown for nickel/-Kieselguhr and nickel/alumina in Table 8. U.S. Pat. No. 4,191,844 discloses that Ni/alumina catalysts "coke" rapidly on reaction with cresols.

Catalytic demethylation of o-cresol occurs at temperatures of about 200° C. to about 450° C., preferably about 250° to about 350° C. o-Cresol is mixed with an excess of hydrogen, preferably at least a 5-fold excess. Optionally, an inert diluent gas, such as helium, nitrogen or water vapor, may also be employed. Catalyst contact time should be at least 0.5 second.

The reaction can be carried out in a conventional reactor, preferably lined with stainless steel or glass, using a fixed or fluidized bed of catalyst. A diluent gas, e.g., water vapor, containing hydrogen in an amount at least equal to the amount stoichiometrically required to convert all of the o-cresol to phenol, may be employed. However, as already noted, use of a diluent is optional and, preferably, the feed is pure hydrogen. Reaction pressure is conveniently atmospheric. Higher pressures can be used, although high pressures tend to result in increased reduction of the aromatic ring.

By separating o-cresol from the mixed phenols, increased conversion to phenol can be achieved. Separation of the demethylation (c), dealkylation (g), to be discussed hereinafter, and isomerization (b) steps allows for selection of catalysts and/or operating conditions which are optimal for each step.

The products from the demethylation step (c) undergo step (d), separation II, e.g., by distillation Phenol and co-products K and A are intermediates for adipic acid manufacture. Co-products benzene and toluene are useful general chemical intermediates and solvents. The resulting o-cresol fraction can be recycled through the demethylation step, i.e., step (c). Resulting m- and/or p-cresols can be recycled through the conversion step, i.e., step (b). Other co-products can be burned as fuel.

Several options exist with regard to the handling of the xylenols and other alkyl phenols from separation I. Selection from among these options will depend upon several factors, including, e.g., the relative amounts of these fractions and the needs of the operator. For example, as illustrated in FIG. 1, the xylenols and other alkyl phenols fraction from separation I can undergo catalytic or thermal dealkylation, step (g), in a procedure similar to the above described demethylation step. The products therefrom can be separated, e.g., in step (d), separation II. The xylenols and other alkyl phenols fractions from separation II can be recycled through the dealkylation step (g); the m and/or p-cresols through the isomerization step (b); and, the o-cresols through the demethylation step (c).

In the embodiment of the invention which comprises carrying the process to adipic acid, the phenol fractions from separations I and II, (which may include K and A from separation II) are reduced to K and A, which are then oxidized to adipic acid, by known techniques. For example, phenol can be reduced by hydrogenation using a nickel catalyst at 150° C. to 250° C. and 5 to 200 atmospheres, and K and A can be oxidized, using nitric acid, at about 50° C. to 150° C.

The process of the invention is preferably carried out in a continuous manner, the various steps being carried out simultaneously.

EXAMPLES

In the following examples which illustrate preferred embodiments of the invention process, Examples 1 to 12 illustrate catalytic demethylation of o-cresol over nickel/silica and/or Kieselguhr catalysts; Example 13 illustrates the superior lifetime of the silica-supported nickel catalysts used in the demethylation step of this invention, compared with alumina-supported nickel catalysts of the art; and Example 14 illustrates the isomerization/transalkylation process step of the invention. Experiments 1 to 13, which are not of the invention, illustrate demethylation of o-cresol over competitive supported nickel catalysts under similar reaction conditions.

In all the examples, temperature is in degrees Celsius. Symbols employed in tabulated examples are as follows: K, cyclohexanone; A, cyclohexanol; Ph, phenol; B, benzene; T, toluene; XYL, xylenols.

Commercial and laboratory-prepared, supported nickel catalysts are tabulated in Tables 2 and 2A. These catalysts were used in Examples 1 to 12 (within the invention) and in Experiments 1 to 13 (outside the invention). For commercial catalysts, nickel contents given as wt % Ni are those supplied by the manufacturer, and gram atomic ratios are calculated assuming compositions to be $Ni/SiO_2$ or $Ni/Al_2O_3$ wherein nickel is fully reduced. For laboratory-prepared catalysts, molar ratios were determined by analysis and wt % Ni was calculated assuming the compositions to be $Ni/SiO_2$, $Ni/SiO_2/Al_2O_3$ or $Ni/Al_2O_3$. In the final column of Table 2, M refers to the Si, Al or Si+Al in the supports of silica (including Kieselguhr), alumina or silica-alumina, respectively.

Commercial catalysts, when supplied in pellet form, were crushed and sieved to a particle size of about 1 mm diameter. Commercial powders were pelletized and then sized to about 1 mm.

TABLE 2

| | Catalyst | | | |
|---|---|---|---|---|
| Example | Catalyst Source | Support | Ni (Wt %) | Gram Atomic Ratio Ni/M |
| 1 | Girdler C150-1-02 | Silica | 50 | 1.0 |
| 2 | Girdler T-1567RS | Kieselguhr | 54.6 | 1.2 |
| 3 | Alfa 89051 | Kieselguhr | 55-60 | 1.4 |
| 4 | Harshaw Ni-0104 | Kieselguhr | 60 | 1.5 |
| 5 | Girdler G-49B | Kieselguhr | 52-54 | 1.2 |
| 6 | Harshaw Ni-0102 | Kieselguhr | 55 | 1.3 |
| 7 | Girdler G-49A | Kieselguhr | 60-64 | 1.7 |
| 8 | United C64-8-01/ C150-1-02 | Silica | 50 | 1.0 |
| 9 | Laboratory prep. | Silica | 79 | 3.9 |
| 10 | Strem 28-143 | Kieselguhr | 60 | 1.5 |
| 11 | Aldrich | Kieselguhr | 60 | 1.5 |
| 12 | Laboratory prep. | Silica-K'guhr | 57 | 1.4 |

TABLE 2A

| | Catalyst | | | |
|---|---|---|---|---|
| Experiment | Catalyst Source | Support | Ni (Wt %) | Gram Atomic Ratio Ni/M |
| 1 | Laboratory prep. | Silica-Alumina | 79 | 3.6 |

TABLE 2A-continued

| Experiment | Catalyst Source | Support | Ni (Wt %) | Gram Atomic Ratio Ni/M |
|---|---|---|---|---|
| 2 | Aldrich | Silica-Alumina | 64 | — |
| 3 | United | Silica-Alumina | 33 | — |
| 4 | Laboratory prep. | Alumina | 93 | 11.6 |
| 5 | Girdler C150-4-03 | Alumina | 60 | 1.3 |
| 6 | Harshaw Ni-0310T | Alumina | 25 | 0.3 |
| 7 | Laboratory prep. | Alumina | 81 | 3.7 |
| 8 | Laboratory prep. | Alumina | 51 | 0.9 |
| 9 | Laboratory prep. | Alumina | 90 | 7.8 |
| 10 | Laboratory prep. | Alumina | 93 | 11.6 |
| 11 | Laboratory prep. | Alumina | 97 | 28.1 |
| 12 | Laboratory prep. | Alumina | 37 | 0.5 |
| 13 | Laboratory prep. | Alumina | 84 | 4.6 |

PROCEDURE FOR LABORATORY PREPARATION OF CATALYSTS FOR EXAMPLE 9

An aqueous solution of nickel nitrate (291 g of Ni(NO$_3$)$_2$.6H$_2$O in 1 L of H$_2$O) was combined with aqueous sodium silicate (28 g of Na$_2$SiO$_3$.9H$_2$O in 500 mL of H$_2$O), and aqueous sodium hydroxide solution (30 g in 300 mL of H$_2$O) was added with stirring at room temperature to give a pH of about 8. The mixture was stirred for several hours and filtered; the product was washed with water, oven-dried for 20 h at 130°, crushed and sieved to a 1 mm particle size. The precatalyst so obtained was converted to catalyst by in situ treatment with hydrogen at about 350°. The catalyst had a Ni/Si gram atomic ratio of 3.9, corresponding to 79 wt % Ni.

FOR EXAMPLE 12

The catalyst of Example 12 was prepared according to Example 1 (catalyst B) of U.S. Pat. No. 4,251,394.

FOR EXPERIMENT 1

1 L of aqueous nickel nitrate solution (244 g of Ni(NO$_3$)$_2$.6H$_2$O per L of water) was combined with aqueous aluminum nitrate solution (31.5 g of Al(NO$_3$)$_3$.9H$_2$O in 100 mL of water) and silicic acid (84 mL of 6 wt % aqueous solution; prepared by acidification of sodium silicate solution). To the mixture was quickly added with stirring at room temperature, 108 mL of concentrated ammonium hydroxide in 100 mL of water, to obtain a mixture having a pH of about 8. The mixture was stirred for several hours and filtered; the product was washed with water, air-dried at 130° for 18 h, sieved to a particle size of 1 mm and reduced in hydrogen. The catalyst had a Ni:Al:Si gram atomic ratio of 8.1:1.3:1, corresponding to 79 wt % Ni, 11 wt % alumina and 10 wt % silica.

FOR EXPERIMENT 10

Nickel nitrate (Ni(NO$_3$)$_2$.6H$_2$O; 580 g) and aluminum nitrate (Al(NO$_3$)$_3$.9H$_2$O; 38 g) were dissolved in 5 L of water. Concentrated ammonium hydroxide (200 mL) was added and the resulting mixture was stirred at room temperature for about 12 h. The precipitate was filtered, washed several times with water, then with acetone, oven-dried at 150°, and finally reduced in hydrogen. The catalyst had a molar Ni/Al ratio of 11.6, corresponding to 93 wt % nickel and 7 wt % alumina.

FOR EXPERIMENTS 4, 7–9 AND 11–13

Catalysts were prepared as described for Experiment 10, except that the proportions of reagents were varied to provide the ultimate nickel contents shown in Table 2A.

PROCEDURE FOR THE CATALYTIC DEMETHYLATION OF O-CRESOL

All commercial catalysts and laboratory-prepared precatalysts were treated in hydrogen in situ before reaction with o-cresol.

Into a stainless steel tubular reactor having an inner diameter to about 7 mm and equipped with a thermocouple was placed commercial catalyst or laboratory-prepared precatalyst. The commercial catalyst or precatalyst was converted to final catalyst (approximately 1 mL) by reduction in hydrogen (40 mL/min) for 2–3 h at about 350°. The temperature was then adjusted to reaction temperature and a mixture of o-cresol and hydrogen, normally 1 mL/h and 1200 mL/h, respectively, was passed through the reactor at atmospheric pressure for 2 to 4 h. Liquid effluent was collected at or below room temperature and analyzed by gas chromatography.

The above general procedure was used in Examples 1 to 12 and Experiments 1 to 13 and the results are tabulated in Tables 3A to 7. The specific reaction conditions used were the following: 300°; 1 atmosphere; o-cresol, 1 cc/h; H$_2$, 20 cc/min; run time, 3 h; catalyst particle size, 0.02–0.6 mm; catalyst vol., ca. 1 mL. Product yields are in mol % of all products and unreacted o-cresol.

TABLE 3A o-Cresol Demethylation Catalyzed by Ni/Silica and/or Kieselguhr

Products and Unreacted o-Cresol, Mol %

| Ex. | Ph | (K + A) | B | T | Cresols o- | Cresols m,p- | XYL | Other Products |
|---|---|---|---|---|---|---|---|---|
| 1 | 56 | 1 | 22 | 4 | 12 | 1 | 0 | 4 |
| 2 | 61 | 0 | 22 | 3 | 10 | 0 | 0 | 4 |
| 3 | 64 | 2 | 18 | 4 | 8 | 2 | 1 | 1 |
| 4 | 55 | 3 | 24 | 4 | 8 | 1 | 0 | 5 |
| 5 | 55 | 0 | 23 | 4 | 14 | 1 | 1 | 2 |
| 6 | 56 | 1 | 21 | 3 | 14 | 1 | 0 | 4 |
| 7 | 47 | 4 | 13 | 4 | 29 | 0 | 2 | 1 |
| 8 | 48 | 0 | 12 | 3 | 28 | 0 | 3 | 6 |
| 9 | 48 | 0 | 34 | 4 | 9 | 2 | 0 | 3 |
| 10 | 37 | 5 | 3 | 1 | 45 | 0 | 6 | 3 |
| 11 | 39 | 2 | 6 | 2 | 45 | 0 | 4 | 2 |
| 12 | 57 | 19 | 3 | 17 | 0 | 1 | 3 | |

TABLE 3B o-Cresol Demethylation over Ni/Silica and/or Kieselguhr

Product Selectivity, Mol %

| Ex. | Support | Conv. (%) | Ph | (K + A) | B | T | Other Products |
|---|---|---|---|---|---|---|---|
| 1 | Silica | 88 | 64 | 1 | 25 | 4 | 6 |
| 2 | Kieselguhr | 90 | 68 | — | 24 | 4 | 4 |
| 3 | Kieselguhr | 92 | 70 | 2 | 19 | 5 | 4 |
| 4 | Kieselguhr | 92 | 60 | 3 | 26 | 4 | 7 |
| 5 | Kieselguhr | 86 | 64 | — | 27 | 4 | 5 |
| 6 | Kieselguhr | 86 | 65 | 1 | 25 | 3 | 6 |
| 7 | Kieselguhr | 71 | 66 | 6 | 18 | 6 | 4 |
| 8 | Silica | 72 | 67 | — | 16 | 5 | 12 |
| 9 | Silica | 91 | 53 | — | 37 | 5 | 5 |
| 10 | Kieselguhr | 55 | 67 | 9 | 6 | 2 | 16 |
| 11 | Kieselguhr | 55 | 71 | 4 | 10 | 4 | 11 |
| 12 | Silica/K'hr | 83 | 69 | 0 | 23 | 3 | 5 |

TABLE 4A o-Cresol Demethylation Catalyzed by Ni/Silica-Alumina
Products and Unreacted o-Cresol, Mol %

| Experiment | Ph | (K + A) | B | T | Cresols o- | Cresols m,p- | XYL | Other Products |
|---|---|---|---|---|---|---|---|---|
| 1 | 51 | 0 | 12 | 2 | 25 | 2 | 2 | 6 |
| 2 | 45 | 6 | 7 | 2 | 33 | 2 | 5 | 0 |
| 3 | 28 | 0 | 3 | 1 | 62 | 0 | 4 | 2 |

TABLE 4B

O-Cresol Demethylation Catalyzed by Ni/Silica-Alumina
Product Selectivity, Mol %

| Experiment | Ni (Wt %) | Conv. (%) | Ph | (K + A) | B | T | Other Products |
|---|---|---|---|---|---|---|---|
| 1 | 79 | 75 | 68 | 0 | 16 | 3 | 13 |
| 2 | 64 | 67 | 67 | 9 | 11 | 3 | 10 |
| 3 | 33 | 38 | 74 | 0 | 8 | 2 | 16 |

TABLE 5A

0-Cresol Demethylation Catalyzed by Ni/Alumina
Products and Unreacted o-Cresol, Mol %

| Experiment | Ph | (K + A) | B | T | Cresols o- | Cresols m,p- | XYL | Other Products |
|---|---|---|---|---|---|---|---|---|
| 4 | 54 | 4 | 6 | 1 | 23 | 6 | 4 | 2 |
| 5 | 36 | 1 | 4 | 1 | 47 | 1 | 9 | 1 |
| 6 | 15 | 0 | 0 | 0 | 78 | 0 | 6 | 1 |
| 7 | 50 | 3 | 14 | 3 | 19 | 4 | 2 | 5 |
| 8 | 33 | 0 | 5 | 1 | 46 | 1 | 12 | 2 |
| 9 | 55 | 4 | 10 | 2 | 18 | 6 | 1 | 4 |
| 10 | 55 | 2 | 8 | 2 | 21 | 6 | 3 | 3 |
| 11 | 48 | 2 | 4 | 1 | 34 | 4 | 6 | 1 |
| 12 | 20 | 0 | 2 | 0 | 61 | 0 | 14 | 3 |
| 13 | 45 | 4 | 8 | 1 | 31 | 3 | 5 | 3 |

TABLE 5B o-Cresol Demethylation Catalyzed by Ni/Alumina
Product Selectivity, Mol %

| Experiment | Ni (Wt %) | Conv. (%) | Ph | (K + A) | B | T | Other Products |
|---|---|---|---|---|---|---|---|
| 4 | 93 | 77 | 70 | 5 | 8 | 1 | 16 |
| 5 | 60 | 53 | 70 | 0 | 7 | 2 | 21 |
| 6 | 25 | 22 | 68 | 0 | 0 | 0 | 32 |
| 7 | 81 | 81 | 62 | 3 | 18 | 3 | 14 |
| 8 | 51 | 54 | 61 | 0 | 9 | 2 | 28 |
| 9 | 90 | 82 | 67 | 5 | 12 | 3 | 13 |
| 10 | 93 | 79 | 70 | 2 | 10 | 3 | 15 |
| 11 | 97 | 66 | 73 | 3 | 6 | 1 | 17 |
| 12 | 37 | 39 | 51 | 0 | 5 | 0 | 44 |
| 13 | 84 | 69 | 65 | 6 | 12 | 1 | 16 |

TABLE 6

Products of o-Cresol Demethylation (Yields, Mol %)

| Product | Ni/Alumina 60% Ni; Exp. 5 (1) | Ni/Alumina 51% Ni; Exp. 8 (2) | Ni/Kieselguhr 55–60% Ni; Ex. 3 | Ni/Silica 50% Ni; Ex. 1 | Ni/Silica-Alumina 64% Ni; Exp. 2 |
|---|---|---|---|---|---|
| Phenol | 36 | 33 | 64 | 56 | 45 |
| Benzene | 4 | 5 | 18 | 22 | 7 |
| Toluene | 1 | 1 | 4 | 4 | 2 |
| K + A | 1 | 0 | 2 | 1 | 6 |
| Xylenols | 9 | 12 | 1 | 0 | 5 |
| m,p-Cresol | 1 | 1 | 2 | 1 | 2 |
| Other Products | 1 | 2 | 1 | 4 | 0 |
| Conv. (%) | 53 | 54 | 92 | 88 | 67 |

TABLE 7

Products of o-Cresol Demethylation (Yields, Mol %)

| Product | Ni/alumina 90% Ni; Exp. 9 | Ni/Kieselguhr 55–60% Ni; Ex. 3 | Ni/silica 50% Ni; Ex. 1 | Ni/Silica-Alumina 79% Ni; Exp. 1 |
|---|---|---|---|---|
| Phenol | 55 | 64 | 56 | 51 |
| Benzene | 10 | 18 | 22 | 12 |
| Toluene | 2 | 4 | 4 | 2 |
| K + A | 4 | 2 | 1 | 0 |
| m,p-Cresol | 6 | 2 | 1 | 2 |
| Xylenols | 1 | 1 | 0 | 2 |
| Other Products | 4 | 1 | 4 | 6 |
| Conv. (%) | 82 | 92 | 88 | 75 |

EXAMPLE 13

Measurement of Catalyst Lifetime

The nickel/Kieselguhr catalyst used in Example 3 and the nickel/alumina catalyst used in Experiment 9 were used to demethylate o-cresol, using procedures described above, but effluent samples were taken after 0.75 h, 3.75 h and, with the nickel/Kieselguhr catalyst, after 11 h of continuous reaction. Conversion of o-cresol is shown in Table 8; the results suggest inferior durability of the alumina-supported catalyst for phenol production.

TABLE 8

Lifetime of Ni Catalysts in o-Cresol Demethylation

| Reaction Time (h) | 0.75 | 3.75 | 11 |
|---|---|---|---|
| Ni/Alumina | | | |
| Conversion (%) | 85 | 77 | — |
| Selectivity to Phenol (mol %) | 59 | 70 | — |
| Ni/Kieselguhr | | | |
| Conversion (%) | 95 | 93 | 90 |
| Selectivity to Phenol (mol %) | 65 | 70 | 67 |

EXAMPLE 14

Isomerization/Transalkylation

In a Hastelloy ®C reactor containing a thermocouple was placed H+-ZSM-5 catalyst (0.8 g, 20–40 mesh, U.S. Sieve Series, about 1.5 cm$^3$). The catalyst was heated to 450° for 30 minutes under a stream of hydrogen gas (20 mL/minute). After lowering the temperature to 400°, m-cresol (1.0 mL/h) was passed with the stream of hydrogen through the reactor at atmospheric pressure for 3 h. Liquid effluent from the reactor was collected at room temperature and analyzed using gas chromatography techniques. The products obtained are reported as mol percent in Table 9.

TABLE 9

| Phenol | 3 |
|---|---|

TABLE 9-continued

| | |
|---|---|
| o-Cresol | 33 |
| m,p-Cresol | 60 |
| Xylenols | 2 |
| Other | 2 |

BEST MODE

The best mode for carrying out the invention is described in the specification and illustrated by Examples 1–9, 12 and 14. Although the preferred embodiments of the invention are described in the above disclosure, it is to be understood that the invention is not limited to the precise constructions disclosed herein, and that the right to all changes and modifications coming within the scope of the following claims is reserved.

I claim:

1. Process for preparing phenol from mixed phenols, which process comprises:
   (a) separating the mixed phenols into at least phenol and o- and m- and/or p-cresols;
   (b) isomerizing m- and/or p-cresols from (a) to o-cresol in a first vessel in the presence of an aluminosilicate zeolite catalyst; and
   (c) demethylating o-cresol from (a) and (b) to phenol in a second vessel in the presence of hydrogen and a catalyst consisting essentially of nickel and silica and/or Kieselguhr having a Ni/Si gram atomic ratio of about 0.2 to about 20 at a temperature of about 200° C. to about 450° C.

2. Process of claim 1 which further comprises:
   (d) separating out phenol, o- and m- and/or p-cresols, xylenols and other alkyl phenols from (c), and in (a), separating the mixture comprising the mixed phenols and the products of (b); in (b), isomerizing m- and/or p-cresols from (a) and (d); and, in (c), demethylating o-cresol from (a) and (d).

3. Process of claim 1, wherein the mixed phenol starting material is produced by depolymerizing polymeric materials having aromatic structures.

4. Process of claim 1 wherein the mixed phenol starting material is produced by depolymerizing peat, coal or lignin.

5. Process of claim 4 wherein the mixed phenol starting material is produced by depolymerizing bituminous, sub-bituminous or lignite coal.

6. Process of claim 4 wherein the mixed phenol starting material is produced by depolymerizing lignin.

7. Process of claim 1 wherein the Ni/Si ratio is about 0.5 to about 5 and the temperature is about 250° C. to about 350° C.

8. Process of claim 7 wherein the Ni/Si ratio is about 1 to about 2.

9. Process of claim 2 which further comprises:
   (e) reducing phenol from (a) and (d) to cyclohexanone/cyclohexanol; and
   (f) oxidizing cyclohexanone/cyclohexanol from (e) to adipic acid.

10. Process of claim 2 which further comprises dealkylating xylenols and other alkyl phenols from (a) and (d).

11. Process of claim 10 which comprises, in (b), isomerizing m- and/or p-cresols from (a) and (d).

12. Process of claim 2 wherein the catalyst in (c) has a Ni/Si gram atomic ratio of about 0.5 to about 5 and the temperature at which (c) is carried out is about 250° C. to about 350° C.

13. Process of claim 12 wherein the catalyst in (c) has a Ni/Si ratio of about 1 to about 2.

14. Process of claim 13 wherein the catalyst in (b) is a ZSM-type catalyst.

15. Process of claim 14 wherein the catalyst is H+-ZSM-5.

16. Process of demethylating o-cresol in the presence of hydrogen and a catalyst consisting essentially of nickel and silica and/or Kieselguhr having a Ni/Si gram atomic ratio of about 0.2 to about 20 at a temperature of about 200° C. to about 450° C.

17. Process of claim 16 wherein the catalyst has a Ni/Si ratio of about 0.5 to about 5 and the temperature is about 250° C. to about 350° C.

18. Process of claim 17 wherein the catalyst has a Ni/Si ratio of about 1 to about 2.

* * * * *

UNITED STATES PATENT AND TRADEMARK OFFICE
CERTIFICATE OF CORRECTION

PATENT NO. : 4,605,790
DATED : August 12, 1986
INVENTOR(S) : Paul W. Wojkowski

It is certified that error appears in the above—identified patent and that said Letters Patent is hereby corrected as shown below:

Column 1, Table 1, second heading, "subbituminous" should be --Subbituminous--.

Column 5, line 39, after "distillation" insert --.--

Column 8, Table 3A, Example 12, "57 19 3 17 0 1 3" should be --57 0 19 3 17 0 1 3--

Column 10, Table 6, last line should read --65  70  67 --.

Signed and Sealed this

Twentieth Day of January, 1987

Attest:

DONALD J. QUIGG

Attesting Officer

Commissioner of Patents and Trademarks